(12) United States Patent
Morimoto

(10) Patent No.: US 9,702,882 B2
(45) Date of Patent: Jul. 11, 2017

(54) METHOD AND SYSTEM FOR ANALYZING MASS SPECTROMETRY DATA

(71) Applicant: SHIMADZU CORPORATION, Kyoto-shi, Kyoto (JP)

(72) Inventor: Kentaro Morimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 500 days.

(21) Appl. No.: 13/656,505

(22) Filed: Oct. 19, 2012

(65) Prior Publication Data

US 2013/0103322 A1    Apr. 25, 2013

(30) Foreign Application Priority Data

Oct. 21, 2011 (JP) .................. 2011-231435

(51) Int. Cl.
```
G01N 33/48      (2006.01)
G01N 33/50      (2006.01)
G01N 33/68      (2006.01)
G06F 19/00      (2011.01)
H01J 49/00      (2006.01)
G06F 19/24      (2011.01)
```

(52) U.S. Cl.
CPC ..... *G01N 33/6848* (2013.01); *G06F 19/3437* (2013.01); *H01J 49/0036* (2013.01); *G06F 19/24* (2013.01)

(58) Field of Classification Search
None
See application file for complete search history.

(56) References Cited

FOREIGN PATENT DOCUMENTS

JP    2007-278712 A    10/2007

OTHER PUBLICATIONS

Ulintz et al. Comparison of MS2-Only, MSA, and MS2/MS3 methodologies for phosphopeptide identification. Journal of Proteome Research, 2009, vol. 8, pp. 887-899.*
"Sequence Query", [online], Matrix Science Ltd., Searched on Aug. 30, 2011.

(Continued)

*Primary Examiner* — Russell S Negin
(74) *Attorney, Agent, or Firm* — Morgan, Lewis & Bockius LLP

(57) ABSTRACT

Provided is a technique for accurately identifying a peptide even if the peptide cannot be identified by MS/MS ion search or de novo sequencing. The technique uses an $MS^n$ spectrum for a low m/z precursor ion. Such a spectrum contains a rather small amount of information, but this information is highly reliable when used for deducing an amino acid sequence by de novo sequencing. Accordingly, an $MS^n$ spectrum for a precursor ion having an m/z value of 500 or less is intentionally obtained, and de novo sequencing is performed on this spectrum to deduce the amino acid sequence covering the range from the m/z of the precursor ion and m/z=0. A highly reliable sequence tag can be generated from the deduced amino acid sequence, the m/z of the precursor ion of the $MS^n$ analysis, and the m/z of the precursor ion of the $MS^2$ analysis.

12 Claims, 8 Drawing Sheets

(56) References Cited

OTHER PUBLICATIONS

"Protein identification System MASCOT Server Version 2.2 Tutorial", [online], Matrix Science Ltd., Searched on Aug. 30, 2011.
Xia Cao et al., "Improved Sequence Tag Generation Method for Peptide Identification in Tandem Mass Spectrometry", J. Proteome Res., 2008, vol. 7(10), pp. 4422-4434.
David L. Tabb et al., "DirecTag: Accurate Sequence Tags from Peptides Ms/MS through Statistical Scoring", Journal of Proteome Research, vol. 7, No. 9, 2008, pp. 3838-3846.
Vlad Zabrouskov et al., "New and Automated $MS^n$ Approaches for Top-Down Identification of Modified Proteins", J Am Soc Mass Spectrom 2005, 16, pp. 2027-2038.
Peiqing Huang et al., "On-line Capillary Liquid Chromatography Tandem Mass Spectrometry on an Ion Trap/Reflectron Time-of-Flight Mass Spectrometer Using the Sequence Tag Database Search Approach for Peptide Sequencing and Protein Identification", J. Am Soc Mass Spectrom 2000, 11, pp. 127-135.
Mikhail M. Savitski et al., "New Data Base-independent, Sequence Tag-based Scoring of Peptide MS/MS Data Validates Mowse Scores, Recovers Below Threshold Data, Singles Out Modified Peptide, and Assesses the Quality of MS/MS Techniques", Molecular & Cellular Proteomics 4.8, pp. 1180-1188.
Examination report received for Japanese Patent Application No. 2011-231435, mailed on Sep. 2, 2014, 4 pages (1 page of English Translation and 3 pages of Official copy).

* cited by examiner

Fig. 3
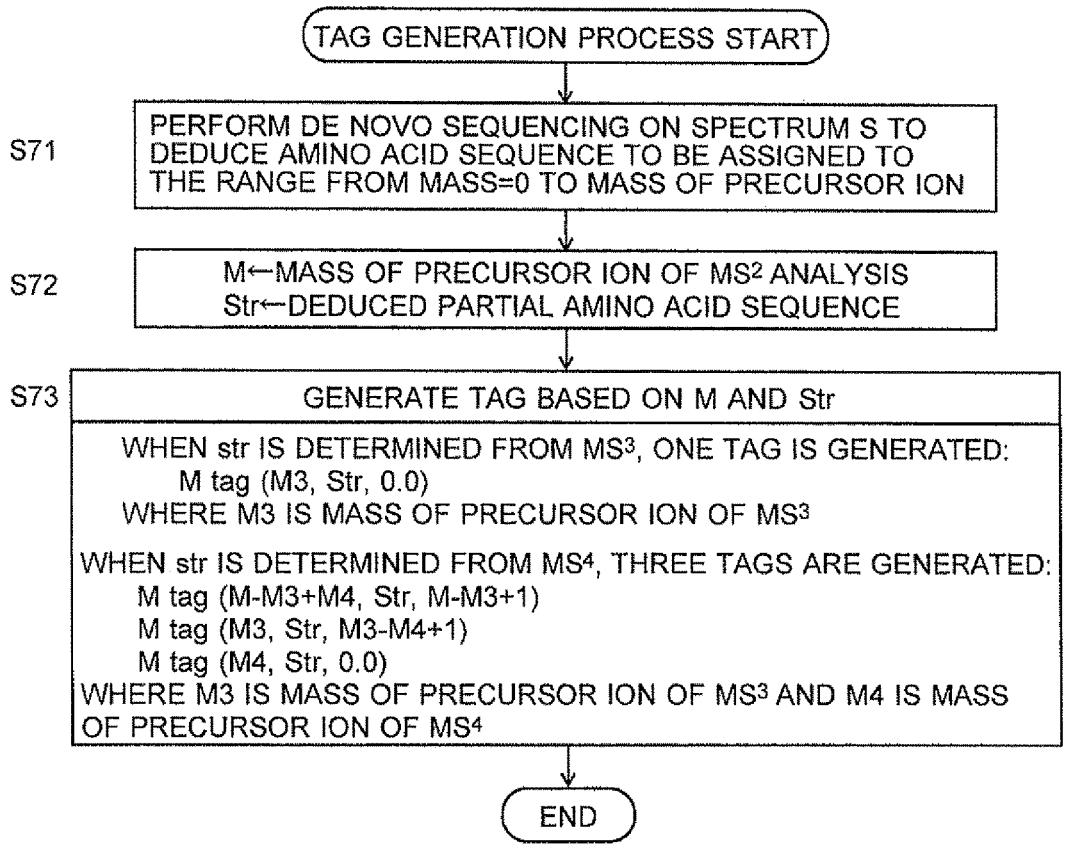
Fig. 4
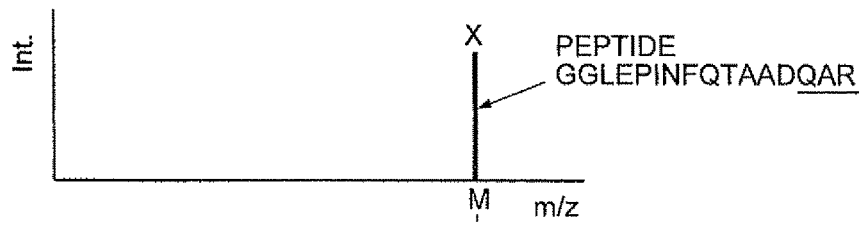
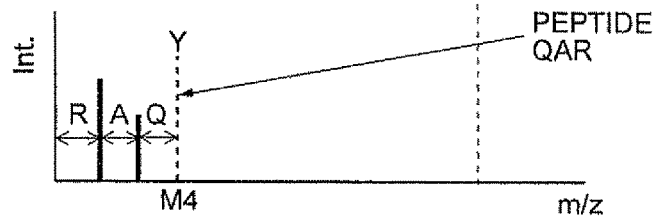

Fig. 5

Mascot Score Histogram

Ions score is -10*Log(P), where P is the probability that the observed match is a random event.
Individual ions scores > 12 indicate identity or extensive homology (p<0.05).
Protein scores are derived from ions scores as a non-probabilistic basis for ranking protein hits.

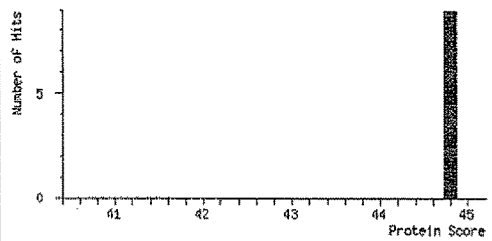

Peptide Summary Report

| Format As | Peptide Summary | | | | | | | | Help |

Significance threshold p< 0.05    Max. number of hits 50
Standard scoring ● MudPIT scoring ○  Ions score or expect cut-off 0    Show sub-sets 0
Show pop-ups ● Suppress pop-ups ○  Sort unassigned Decreasing Score    Require bold red ☐

[Select All] [Select None] [Search Selected] [Archive Report]

1. KATL2_MOUSE   Mass: 61514   Score: 45   Matches: 1(1)   Sequences: 1(1)
   Katanin p80 ATPase-containing subunit A-like 2 OS=Mus musculus GN=Katnal2 PE=2 SV=2
   ☐ Check to include this hit in error tolerant search or archive report

| Query | Observed | Mr(expt) | Mr(calc) | Delta | Miss | Score | Expect | Rank | Unique | Peptide |
   |---|---|---|---|---|---|---|---|---|---|---|
   | 1 | 1687.9400 | 1686.9327 | 1686.9053 | 0.0274 | 1 | 45 | 3.3e-005 | 1 | U | M.ELSYQTLKLTHQAR.E |

2. PKP4_HUMAN   Mass: 134985   Score: 45   Matches: 1(1)   Sequences: 1(1)
   Plakophilin-4 OS=Homo sapiens GN=PKP4 PE=1 SV=1
   ☐ Check to include this hit in error tolerant search or archive report

| Query | Observed | Mr(expt) | Mr(calc) | Delta | Miss | Score | Expect | Rank | Unique | Peptide |
   |---|---|---|---|---|---|---|---|---|---|---|
   | 1 | 1687.9400 | 1686.9327 | 1686.9053 | 0.0275 | 1 | 45 | 3.3e-005 | 1 | U | R.NLSYRLELEVPGAR.L |

Proteins matching the same set of peptides:
   PKP4_MOUSE   Mass: 192268   Score: 45   Matches: 1(1)   Sequences: 1(1)
   Plakophilin-4 OS=Mus musculus GN=Pkp4 PE=1 SV=1

3. NDC80_MACFA   Mass: 74335   Score: 45   Matches: 1(1)   Sequences: 1(1)
   Kinetochore protein NDC80 homolog OS=Macaca fascicularis GN=NDC80 PE=2 SV=1
   ☐ Check to include this hit in error tolerant search or archive report

| Query | Observed | Mr(expt) | Mr(calc) | Delta | Miss | Score | Expect | Rank | Unique | Peptide |
   |---|---|---|---|---|---|---|---|---|---|---|
   | 1 | 1687.9400 | 1686.9327 | 1686.8424 | 0.0903 | 1 | 45 | 3.3e-005 | 1 | U | K.ELLNETEEEINKAR.N |

4. OVAL_CHICK   Mass: 43186   Score: 45   Matches: 1(1)   Sequences: 1(1)
   Ovalbumin OS=Gallus gallus GN=SERPINB14 PE=1 SV=2
   ☐ Check to include this hit in error tolerant search or archive report

| Query | Observed | Mr(expt) | Mr(calc) | Delta | Miss | Score | Expect | Rank | Unique | Peptide |
   |---|---|---|---|---|---|---|---|---|---|---|
   | 1 | 1687.9400 | 1686.9327 | 1686.8325 | 0.1002 | 0 | 45 | 3.3e-005 | 1 | U | R.GGLEPINFQTAADQAR.E |

5. TDRD3_XENTR   Mass: 79895   Score: 45   Matches: 1(1)   Sequences: 1(1)
   Tudor domain-containing protein 3 OS=Xenopus tropicalis GN=tdrd3 PE=2 SV=2
   ☐ Check to include this hit in error tolerant search or archive report

Fig. 8

Mascot Score Histogram

Ions score is -10*Log(P), where P is the probability that the observed match is a random event.
Individual ions scores > 13 indicate identity or extensive homology (p<0.05).
Protein scores are derived from ions scores as a non-probabilistic basis for ranking protein hits.

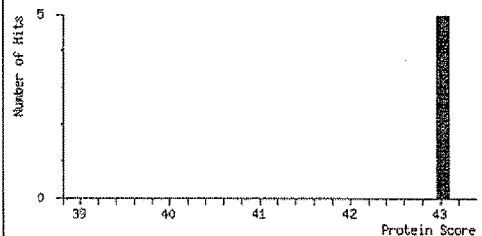

Peptide Summary Report

Format As: Peptide Summary                                                                 Help Significance threshold p< 0.05    Max. number of hits 50
Standard scoring ⊙ MudPIT scoring ○  Ions score or expect cut-off 0   Show sub-sets 0
Show pop-ups ⊙ Suppress pop-ups ○  Sort unassigned Decreasing Score   Require bold red □

[Select All] [Select None] [Search Selected] [Archive Report]

1.   ALBU_BOVIN   Mass: 71244   Score: 43   Matches: 1(1)   Sequences: 1(1)
     Serum albumin OS=Bos taurus GN=ALB PE=1 SV=4
     ☐ Check to include this hit in error tolerant search or archive report Query  Observed  Mr(expt)  Mr(calc)  Delta  Miss Score  Expect  Rank Unique  Peptide
       1    927.5000  926.4927  926.4861  0.0066   0    43   5.5e-005  1      U    K.YLYEIAR.R Proteins matching the same set of peptides:
     ALBU_FELCA   Mass: 70611   Score: 43   Matches: 1(1)   Sequences: 1(1)
     Serum albumin OS=Felis catus GN=ALB PE=1 SV=1
     ALBU_PIG     Mass: 71643   Score: 43   Matches: 1(1)   Sequences: 1(1)
     Serum albumin OS=Sus scrofa GN=ALB PE=1 SV=2
     FETA_HORSE   Mass: 70130   Score: 43   Matches: 1(1)   Sequences: 1(1)
     Alpha-fetoprotein OS=Equus caballus GN=AFP PE=2 SV=1
     ALBU_CANFA   Mass: 70556   Score: 41   Matches: 1(1)   Sequences: 1(1)
     Serum albumin OS=Canis familiaris GN=ALB PE=1 SV=3

2.   FETA_CANFA   Mass: 70563   Score: 43   Matches: 1(1)   Sequences: 1(1)
     Alpha-fetoprotein OS=Canis familiaris GN=AFP PE=2 SV=1
     ☐ Check to include this hit in error tolerant search or archive report Query  Observed  Mr(expt)  Mr(calc)  Delta  Miss Score  Expect  Rank Unique  Peptide
       1    927.5000  926.4927  926.4861  0.0066   0    43   5.5e-005  1      U    R.YIYEIAR.R Proteins matching the same set of peptides:
     FETA_PIG     Mass: 70405   Score: 43   Matches: 1(1)   Sequences: 1(1)
     Alpha-fetoprotein OS=Sus scrofa GN=AFP PE=2 SV=1
     FETA_BOVIN   Mass: 70368   Score: 43   Matches: 1(1)   Sequences: 1(1)
     Alpha-fetoprotein OS=Bos taurus GN=AFP PE=2 SV=1

3.   USH1C_BOVIN  Mass: 62254   Score: 43   Matches: 1(1)   Sequences: 1(1)
     Harmonin OS=Bos taurus GN=USH1C PE=2 SV=1
     ☐ Check to include this hit in error tolerant search or archive report Query  Observed  Mr(expt)  Mr(calc)  Delta   Miss Score  Expect  Rank Unique  Peptide
       1    927.5000  926.4927  926.5185  -0.0258   0    43   5.5e-005  1      U    K.LVINEPSR.L

METHOD AND SYSTEM FOR ANALYZING MASS SPECTROMETRY DATA

TECHNICAL FIELD

The present invention relates to a method and system for processing and analyzing mass spectrometry data obtained by an $MS^n$ analysis on a peptide or similar high-molecular compound originating from a living organism, to identify the high-molecular compound or analyze its structure.

BACKGROUND ART

In recent years, structural and functional analyses of proteins have been rapidly promoted as post-genome research. As one method for such structural and functional analyses of proteins (proteome analyses), an expression analysis or primary structure analysis of a protein using a mass spectrometer has been widely performed in recent years. In this context, a so-called $MS^n$ analysis, which includes the steps of capturing a specific kind of ion and dissociating the ion by collision induced dissociation (CID) or similar process within a quadrupole ion trap or the like, has proven itself to be a powerful technique.

A general process of identifying a protein by $MS^n$ analysis is as follows: A sample of the protein is broken into peptide fragments by a chemical process or enzymatic digestion. The obtained mixture of peptide fragments is subjected to mass spectrometry to obtain a mass spectrum ($MS^1$ spectrum). Subsequently, from the mass spectrum data of the mixture of the peptide fragments, a group of isotope peaks originating from a single peptide are selected as precursor ions. Then, these precursor ions are dissociated into fragment ions by CID, and a mass spectrometry of these fragment ions, i.e. the $MS^2$ analysis, is performed. By the CID process, the amino acid sequence making up a specific peptide has its bonds broken at various positions, being divided into fragments having different amino acid residues. Therefore, the obtained $MS^2$ spectrum reflects the amino acid sequence of that specific peptide.

That is to say, the distances of the peaks on the $MS^2$ spectrum correspond to the molecular weights of the amino acid residues. Therefore, it is possible to determine the amino acid sequence from the distances of those peaks. A partial amino acid sequence of the original peptide can be obtained by extracting a sequence tag (i.e. a tag showing a continuous amino acid sequence that can exist in a peptide or protein) from the $MS^2$ spectrum. Furthermore, by subjecting this partial amino acid sequence to an amino acid sequence homology search, such as BLAST® (Basic Local Alignment Search Tool), the protein can be identified. The aforementioned technique of obtaining a partial amino acid sequence of a peptide is called "de novo sequencing" and is widely used.

In another technique, called the "MS/MS ion search", the protein is directly identified from the $MS^2$ spectrum by using the mass-to-charge ratios (m/z) of fragment ions (product ions). In the MS/MS ion search, the identification process relies on the statistical determination of the degree of coincidence between an $MS^2$ spectrum obtained by an actual measurement and a virtual CID spectrum created in a computer by calculating the distribution of the mass-to-charge ratios of peptide fragments obtained by digesting each and every protein registered in a database with the same enzyme. An expected value indicating the reliability of the degree of coincidence is also calculated from the molecular weight information of the peptides. Commonly known examples of the tools for the MS/MS ion search are "X!Tandem", which is a piece of open source software, and "Mascot MS/MS ion search", which is a product of the British manufacturer Matrix Science Ltd.

To identify proteins, the BLAST system uses only the information of character strings representing amino acid sequences, while the MS/MS ion search uses only the information of the mass-to-charge ratios of product ions. Another searching tool, called the "Sequence Tag search", identifies proteins by using these types of information in a combined form. Similar to the MS/MS ion search, the Sequence Tag search includes attempting identification of a peptide based on the virtual CID spectra of proteins registered in a database and the already revealed amino acid sequence information, and showing the result. One commonly known example of the tools for the Sequence Tag search is the "Mascot Sequence Query", which is also a product of Matrix Science Ltd (see Non-Patent Document 1). The database search setting screen of Mascot Sequence Query is similar to that of Mascot MS/MS ion search; a difference exists in that a sequence tag is used as input data in place of a list of peaks collected from an $MS^2$ spectrum (see Non-Patent Document 2).

For example, the tags used in the Sequence Tag search look like "M tag (M1, Str, M2)", where M is the mass-to-charge ratio of the precursor ion of the $MS^2$ analysis, M1 is the mass of one ion P1 in the $MS^2$ spectrum, M2 is the mass of another ion P2 in the $MS^2$ spectrum, and Str is a partial amino acid sequence corresponding to the difference between the two ions P1 and P2. That is to say, the Sequence Tag search uses the mass-to-charge ratio of the precursor ion, the partial amino acid sequence as well as the mass-to-charge ratios of the peaks at the starting and ending points of the partial amino acid sequence to identify the peptide. As compared to the MS/MS ion search, the Sequence Tag search is characterized in that the peptide can be identified with high reliability even from a small number of peaks. As compared to BLAST, the characteristic exists in that the protein can be identified even from a shorter amino acid sequence.

As just described, the Sequence Tag search is an effective technique for protein identification. However, to ensure its high identification accuracy, a highly reliable sequence tag must be given to the system. To address this problem, several methods for generating sequence tags for peptide identification have been proposed in recent years. For example, in a method described in Non-Patent Document 3, any ion peaks other than the ions corresponding to the $b^+$, $y^+$, $b^{++}$ and $y^{++}$ fragments are removed from an $MS^2$ spectrum obtained by an $MS^2$ analysis of a triply-charged peptide. In other words, any ion peaks other than the ions forming either a singly charged or doubly charged pair are removed. Then, on the assumption that the remaining peaks are highly reliable, one or more sequence tags that can be derived from these peaks are listed as possible choices. Several other methods for generating sequence tags based on an $MS^2$ spectrum have also been proposed. However, it is not always easy to assuredly obtain highly reliable sequence tags, because the S/N ratio of $MS^2$ spectra is generally low and the peaks of the product ions are often prevented from being clearly observable.

BACKGROUND ART DOCUMENT

Non-Patent Document

Non-Patent Document 1: "Sequence Query", [online], Matrix Science Ltd., [Searched on Aug. 30, 2011], Internet Non-Patent Document 2: "Protein Identification System MASCOT Server Version 2.2 Tutorial", [online], Matrix Science Ltd., [Searched on Aug. 30, 2011], Internet Non-Patent Document 3: Xia Cao et al., "Improved Sequence Tag Generation Method for Peptide Identification in Tandem Mass Spectrometry", *J. Proteome Res.*, 2008, Vol. 7(10), pp. 4422-4434

SUMMARY OF THE INVENTION

Problem to be Solved by the Invention

The present invention has been developed in view of the previously described problem, and its primary objective is to provide a method and system for analyzing mass spectrometry data by which peptides or proteins can be identified with high accuracy by improving the reliability of the sequence tags in the process of identifying proteins by sequence tag search.

Means for Solving the Problems

To deduce a portion of an amino acid sequence based on an $MS^2$ spectrum by the aforementioned "de novo sequencing", it is necessary to identify the starting and ending peaks respectively corresponding to the two ends of the sequence. However, in many cases, since $MS^2$ spectra have unnecessary peaks appearing due to various reasons, automatic identification of the starting and ending peaks from an $MS^2$ spectrum is difficult, so that it is almost impossible to conduct an accurate sequencing. Generally, a partial amino acid sequence can be correctly deduced only when the amino acid sequence has been fully determined, with no lack of product ions, within a range from the mass-to-charge ratio of the precursor ion to the zero point of the mass-to-charge ratio by correcting the mass-to-charge ratio of the terminus of the amino acid sequence; such deduction is normally possible only when the precursor ion has a low mass-to-charge ratio. "Correcting the mass-to-charge ratio of the terminus of the amino acid sequence" means the correction of the mass-to-charge ratio of H or $OH_3$ to be added to an N or C terminus of the peptide. The difference in mass-to-charge ratio between a given pair of peaks corresponds to the mass of an amino acid residue, while the difference between a given peak and the zero point of the mass-to-charge ratio corresponds to the sum of the mass of an amino acid residue and that of H or $OH_3$. Similarly, the difference in the mass-to-charge ratio between a given peak and the precursor ion corresponds to the sum of the mass of an amino acid residue and that of H or $OH_3$.

$MS^n$ spectra obtained by repeating the selection and dissociation of the ions up to n=3 or greater generally have good S/N ratio and clearly show the peaks of the product ions. The precursor ion used in such an $MS^n$ analysis merely corresponds to a portion of the amino acid sequence of the original peptide. However, since the number of product ions produced by the dissociation of this precursor ion is small, the deduction of the amino acid sequence by de novo sequencing is highly reliable. In particular, when the mass-to-charge ratio of the precursor ion is small (i.e. approximately 500 Da or less in most cases), the number of amino acid residues making up the ion is considerably low (e.g. within a range from two to four), so that the amino acid sequence of the ion can be deduced with high reliability by de novo sequencing. Thus, it can be said that an $MS^n$ spectrum obtained from a low-mass precursor ion is not suitable for directly deducing the amino acid sequence of the entire length of the peptide, but is suitable for accurately deducing a partial amino acid sequence. Focusing on this point, the present inventor has conceived the idea of preferentially dissociating a low-mass ion (though low-mass ions have conventionally been regarded as less important), performing de novo sequencing on the obtained $MS^n$ spectrum to accurately determine the amino acid sequence of the precursor ion, and using this amino acid sequence as a sequence tag.

The first aspect of the present invention aimed at solving the aforementioned problem provides a mass spectrometry data analyzing method for identifying a protein in a test sample, using data collected by performing a mass spectrometry of the test sample, including:

a) a partial amino acid sequence deducing step, in which de novo sequencing on an $MS^n$ spectrum (where n is an integer equal to or greater than three) obtained by performing an $MS^n$ analysis on the test sample is performed to determine a partial amino acid sequence;

b) a tag generating step, in which a sequence tag is generated by using the mass-to-charge ratio of a precursor ion of the $MS^2$ analysis, the mass-to-charge ratio of a precursor ion of the $MS^n$ analysis, and the partial amino acid sequence determined in the partial amino acid sequence deducing step; and c) a database searching step, in which a database of amino acid sequence information of proteins is searched for a protein that matches the information represented by the sequence tag.

As in the normal mode of protein identification, the test sample is a peptide mixture prepared by breaking a protein into fragments by enzymatic digestion or other processes. This mixture may possibly contain an insufficiently digested protein (i.e. a piece of protein having an extremely long amino acid sequence). In such a case, as compared to the entire length of the amino acid, the partial amino acid sequence represented by the sequence tag may be too short to sufficiently narrow down the kinds of peptides by the method according to the first aspect of the present invention. In such a case, it is preferable to use the information of the mass-to-charge ratios of all the precursor ions selected in the plural stages of the dissociating operation.

Thus, the second aspect of the present invention aimed at solving the aforementioned problem provides a mass spectrometry data analyzing method for identifying a protein in a test sample, using data collected by performing a mass spectrometry of the test sample, including:

a) a partial amino acid sequence deducing step, in which de novo sequencing on an $MS^n$ spectrum (where n is an integer equal to or greater than three) obtained by performing an $MS^n$ analysis on the test sample is performed to determine a partial amino acid sequence;

b) a tag generating step, in which a sequence tag is generated by using the mass-to-charge ratios of precursor ions used in $MS^m$ analyses (where m is all integers equal to or greater than two and equal to or less than n) and the partial amino acid sequence determined in the partial amino acid sequence deducing step; and c) a database searching step, in which a database of amino acid sequence information of proteins is searched for a protein that matches the information represented by the sequence tag.

The third aspect of the present invention aimed at solving the aforementioned problem provides a system for carrying out the method according to the first aspect of the present invention, that is, a mass spectrometry data analyzing system for identifying a protein in a test sample, using data collected by performing a mass spectrometry of the test sample, including:

a) a partial amino acid sequence deducing section for performing de novo sequencing on an $MS^n$ spectrum (where n is an integer equal to or greater than three) obtained by performing an $MS^n$ analysis on the test sample, to determine a partial amino acid sequence;

b) a tag generating section for generating a sequence tag by using the mass-to-charge ratio of a precursor ion of the $MS^2$ analysis, the mass-to-charge ratio of a precursor ion of the $MS^n$ analysis, and the partial amino acid sequence determined by the partial amino acid sequence deducing section; and c) a database searching section for searching a database of amino acid sequence information of proteins for a protein that matches the information represented by the sequence tag.

The fourth aspect of the present invention aimed at solving the aforementioned problem provides a system for carrying out the method according to the second aspect of the present invention, that is, a mass spectrometry data analyzing method for identifying a protein in a test sample, using data collected by performing a mass spectrometry of the test sample, including:

a) a partial amino acid sequence deducing section for performing de novo sequencing on an $MS^n$ spectrum (where n is an integer equal to or greater than three) obtained by performing an $MS^n$ analysis on the test sample, to determine a partial amino acid sequence;

b) a tag generating section for generating a sequence tag by using the mass-to-charge ratios of precursor ions used in $MS^m$ analyses (where m is all integers equal to or greater than two and equal to or less than n) and the partial amino acid sequence determined by the partial amino acid sequence deducing section; and c) a database searching section for searching a database of amino acid sequence information of proteins for a protein that matches the information represented by the sequence tag.

In the mass spectrometry data analyzing methods and systems according to the first through fourth aspects of the present invention, an $MS^n$ spectrum obtained from a precursor ion having a relatively low mass-to-charge ratio is subjected to de novo sequencing to obtain partial amino acid sequence information, despite the fact that such an ion produces only a small number of kinds of product ions and, in that sense, does not provide much information. In deducing an amino acid sequence from the $MS^n$ spectrum, the de novo sequencing may preferably be performed over a range starting from the mass-to-charge ratio of the precursor ion in the $MS^n$ spectrum and ending at the zero point of the mass-to-charge ratio. That is to say, the de novo sequencing should be performed so as to determine an amino acid sequence that can cover all the product ions produced from the precursor ion. An $MS^n$ spectrum obtained in the previously described manner is most likely to show clear peaks of the product ions and few noise peaks. Therefore, by the de novo sequencing, a partial amino acid sequence can be obtained with high reliability.

The clear knowledge of the mass-to-charge ratios at the starting and ending points of the process of determining the amino acid sequence by de novo sequence, together with the knowledge of either the mass-to-charge ratio of the precursor ion of the $MS^2$ analysis or the mass-to-charge ratio of the precursor ion of each of the multiple stages of ion dissociation, ensures the sequence tags generated from these pieces of information are highly reliable. Using such reliable sequence tags improves the accuracy of identifying peptides or proteins by the sequence tag search.

Even when no amino acid sequence that can cover all the product ions can be uniquely identified by the de novo sequencing based on the $MS^n$ spectrum, i.e. even if some portion of the amino acid remains unidentified, it is in some cases possible to uniquely determine the amino acid sequence of the concerned peptide by using an amino acid sequence deduced, for example, from another $MS^n$ spectrum.

Accordingly, in one preferable mode of the first or second aspect of the present invention, the partial amino acid sequence deducing step includes determining a plurality of partial amino acid sequences by performing de novo sequencing on each of a plurality of $MS^n$ spectra respectively obtained for two or more different precursor ions, the tag generating step includes generating a plurality of sequence tags respectively corresponding to the partial amino acid sequences determined in the partial amino acid sequence deducing step, and the database searching step includes searching for a protein by a database search using the plurality of sequence tags.

A study by the present inventor has revealed that, in order to accurately deduce the partial amino acid sequence, the precursor ion of the $MS^n$ spectrum to be used for the de novo sequencing should preferably have a mass-to-charge ratio corresponding to an amino acid sequence consisting of four or less residues. This is approximately 500 Da or less in terms of mass-to-charge ratio. Accordingly, an appropriate $MS^n$ spectrum can be obtained by repeating the dissociation of the ions until an ion which satisfies this condition, and which has an appropriate intensity as a precursor ion, is detected.

Effect of the Invention

By the mass spectrometry data analyzing methods and systems according to the first through fourth aspects of the present invention, a highly reliable sequence tag for deducing the entire amino acid sequence of a peptide can be generated by obtaining a partial amino acid sequence of a precursor ion of an $MS^2$ analysis, based on an $MS^n$ spectrum obtained by repeating the selection and dissociation of precursor ions. In particular, when an amino acid sequence covering the range from the mass-to-charge ratio of the precursor ion to the zero point of the mass, with the correction of the termini of the amino acid taken into account, has been successfully determined for an $MS^n$ spectrum, the amino acid sequence is extremely reliable, and therefore, the sequence tag can be regarded as correct. A sequence tag search is characterized in that the search result is always correct as long as the sequence tag is correct and the intended protein is registered in the database used for the search. Even when the peptide cannot be correctly identified with high reliability by the de novo sequencing on an $MS^2$ spectrum or the MS/MS ion search, it is still possible to correctly identify the protein (peptide) or appropriately narrow down the peptide candidates by performing the sequence tag search using the highly reliable sequence tag obtained in the previously described manner. In particular, even if the peptide candidates cannot be automatically narrowed down to one candidate, those candidates always include the correct peptide (i.e. no false-positive error will occur). Thus, the present invention is effective for avoiding the miss of identification.

BRIEF DESCRIPTION OF THE DRAWINGS

FIG. 3 is a flowchart showing the detailed steps of the tag generation process in FIG. 2.

FIG. 4 is a schematic chart showing the relationship between a precursor ion of an $MS^2$ analysis and an amino acid sequence derived from an $MS^n$ spectrum.

FIG. 5 is a screen shot showing a list of peptide candidates selected by "Mascot Sequence Query" using a sequence tag generated from the $MS^4$ spectrum shown in FIG. 6.

FIG. 8 is a screen shot showing a list of peptide candidates selected by "Mascot Sequence Query" using a sequence tag generated from the $MS^3$ spectrum shown in FIG. 7.

BEST MODE FOR CARRYING OUT THE INVENTION

Figure 1:
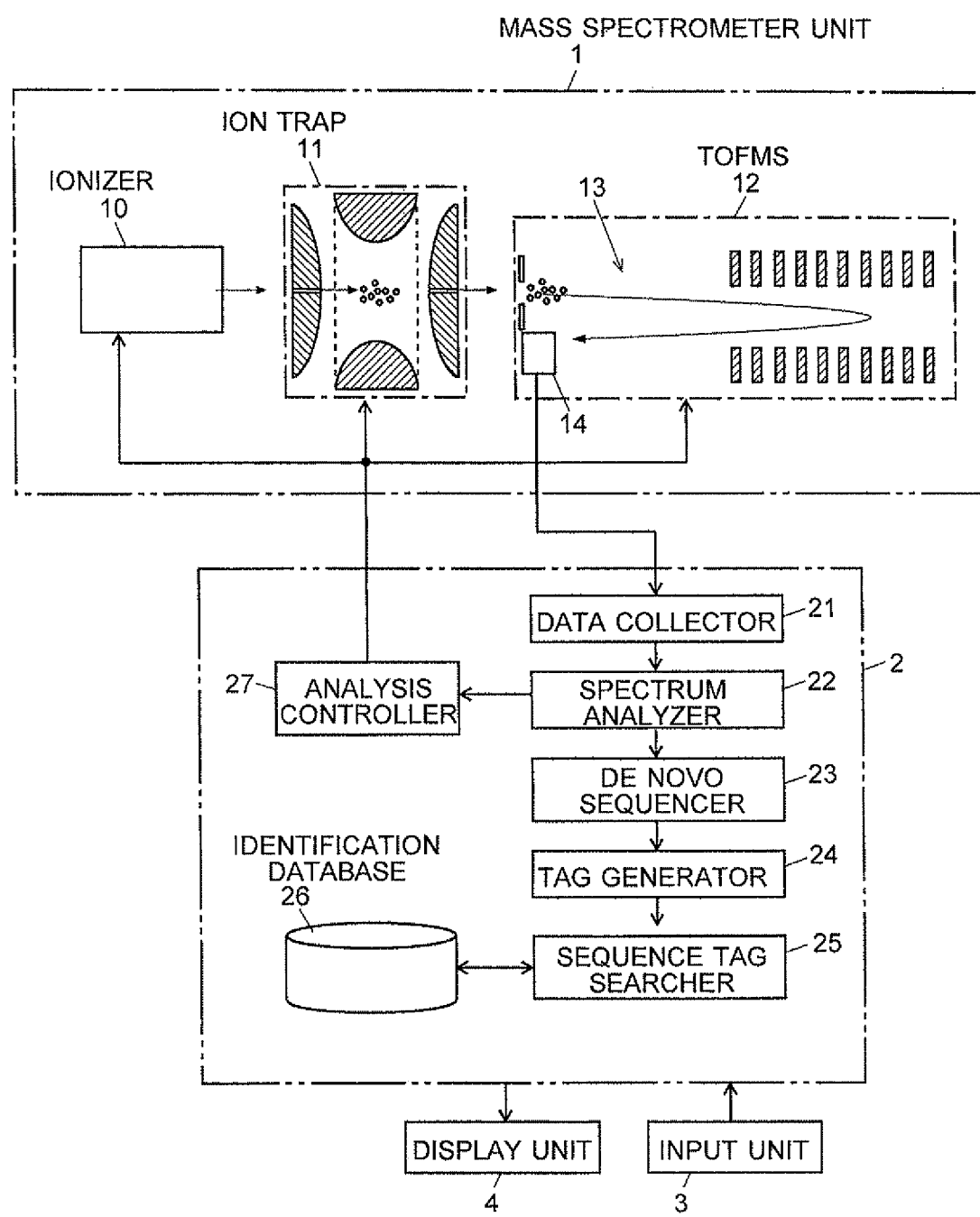
FIG. 1 is an overall configuration diagram of one embodiment of a peptide analyzing system including a mass spectrometry data analyzing system according to the present invention.

One embodiment of a peptide analyzing system including a mass spectrometry data analyzing system according to the present invention is hereinafter described with reference to the attached drawings. FIG. 1 is an overall configuration diagram of the peptide analyzing system of the present embodiment.

The peptide analyzing system of the present embodiment mainly consists of a mass spectrometer unit 1 and a controlling and processing unit 2, the latter unit being composed of a computer and other elements. The mass spectrometer unit 1 is a quadrupole ion trap time-of-flight mass spectrometer including: an ionizer 10, in which the molecules or atoms in a sample to be analyzed are ionized by matrix assisted laser desorption ionization (MALDI) or electrospray ionization (ESI); a three-dimensional quadrupole ion trap 11, which can select ions according to their mass-to-charge ratios (m/z) and breaks them into fragments by CID; and a time-of-flight mass spectrometer (TOFMS) 12, in which various kinds of ions collectively ejected from the ion trap 11 are separated and detected according to their mass-to-charge ratios. The time-of-flight mass spectrometer 12 includes a reflectron-type flight space 13 for making the flying ions turn around by a direct-current electric field generated by a reflector, and an ion detector 14 for sequentially detecting the ions which have been temporally separated according to their mass-to-charge ratios while travelling in the flight space 13.

The controlling and processing unit 2 has an analysis controller 27 for controlling each component of the mass spectrometer unit 1, a data collector 21 for digitizing, collecting and storing detection signals fed from the ion detector 14, a spectrum analyzer 22 for creating an $MS^n$ spectrum from the collected data, a de novo sequencer 23 for performing a de novo sequencing on the $MS^n$ spectrum data, a tag generator 24 for generating a sequence tag from a partial amino acid sequence determined by de novo sequencing and the mass-to-charge ratio of a precursor ion, a sequence tag searcher 25 for identifying a peptide in a test sample by a database search using the sequence tag, and an identification database (DB) 26 in which identification information to be used for deducing amino acid sequences of proteins (peptides) is previously stored. An input unit 3 for allowing users to enter or set search conditions or perform necessary operations for spectrum analysis, and a display unit 4 for showing a screen for setting and entering search conditions or displaying the result of identification, are connected to the controlling and processing unit 2. The functions of the sequence tag searcher 25 can be realized by commonly used search engine software, such as the aforementioned "Mascot Sequence Query."

A data-analyzing process for identifying a peptide by the peptide analyzing system of the present embodiment is hereinafter described with reference to the flowchart shown in FIG. 2.

An analysis operator prepares a test sample containing peptide fragments, by digesting a protein in question by means of an appropriate enzyme, e.g. trypsin (Step S1). When the analyzing process is initiated, the analysis controller 27 initially sets parameter n to 2, which indicates the number of stages of dissociation, and operates the mass spectrometer unit 1 to perform an $MS^n$ analysis for the test sample (Step S2). When Step S2 is performed for the first time, the mass spectrometer unit 1 under the control of the analysis controller 27 performs an $MS^2$ analysis.

That is to say, an $MS^1$ analysis of the test sample is initially performed, after which the spectrum analyzer 22 creates an $MS^1$ spectrum from the data collected by the data collector 21. On this $MS^1$ spectrum, the spectrum analyzer 22 locates an ion peak originating from a single peptide and selects it as the precursor ion for an $MS^2$ analysis. Subsequently, under the control of the analysis controller 27, the mass spectrometer unit 1 performs the $MS^2$ analysis of the selected precursor ion. In detail, various kinds of ions generated from the test sample in the ionizer 10 are temporarily captured in the ion trap 11. In this ion trap 11, a kind of ion having the mass-to-charge ratio of the precursor ion is exclusively selected and then dissociated by CID. During this process, the amino acid sequence making up the single peptide concerned has its bonds broken at various positions, producing various amino acid residues captured as the product ions within the ion trap 11. These product ions are collectively ejected from the ion trap 11 and subjected to mass spectrometry by the time-of-flight mass spectrometer 12. The data collector 21 collects data obtained by the $MS^2$ analysis. The spectrum analyzer 22 creates an $MS^2$ spectrum from the collected data.

Then, the spectrum analyzer 22 determines whether an ion peak having a mass-to-charge ratio equal to or lower than 500 Da and an intensity equal to or higher than a specific level can be found in the obtained $MS^2$ spectrum (Step S3). The determination criterion of 500 Da is the condition for determining whether the number of amino acid residues making up the concerned precursor ion is as small as two through four. When the precursor ion is composed of such a small number of amino acid residues, the spectrum of the product ions produced by dissociating the precursor ion will be so simple that the amino acid sequence from the mass-to-charge ratio of that precursor ion to the zero point of the mass (m/z=0) can be determined with considerably high accuracy by de novo sequencing. The determination criterion of 500 Da may be appropriately changed, when necessary. However, setting a higher criterion makes the MS$^n$ spectrum more complex and lowers the probability of successful determination of the amino acid sequence by de novo sequencing. Setting a lower criterion decreases the number of amino acid residues. Although this ensures the correctness of the sequence tag, it also makes difficult the operation of narrowing the peptide candidates down to a practically small number. Accordingly, using a mass-to-charge ratio value within a range from 400 to 600 Da is appropriate for the determination in Step S3.

If no ion peak having a mass-to-charge ratio equal to or lower than 500 Da and an intensity equal to or higher than a specific level can be found in the MS$^2$ spectrum, the parameter n is incremented by one (Step S9), after which an ion having a high intensity in the MS$^2$ spectrum is selected as a new precursor ion (Step S10) and the operation returns to Step S2. In other words, when the result of determination for the MS$^2$ spectrum in Step S3 has turned out to be "No", an ion having a high intensity in the MS$^2$ spectrum is selected as a new precursor ion and an MS$^3$ analysis using this precursor ion is performed to obtain an MS$^3$ spectrum. In Step S10, an ion having the highest intensity in the spectrum can be typically selected as the precursor ion. However, this is not mandatory; for example, if the presence of an impurity having a known mass-to-charge ratio is previously known, the impurity can be excluded from the selection of the ion having the highest intensity.

Figure 2:
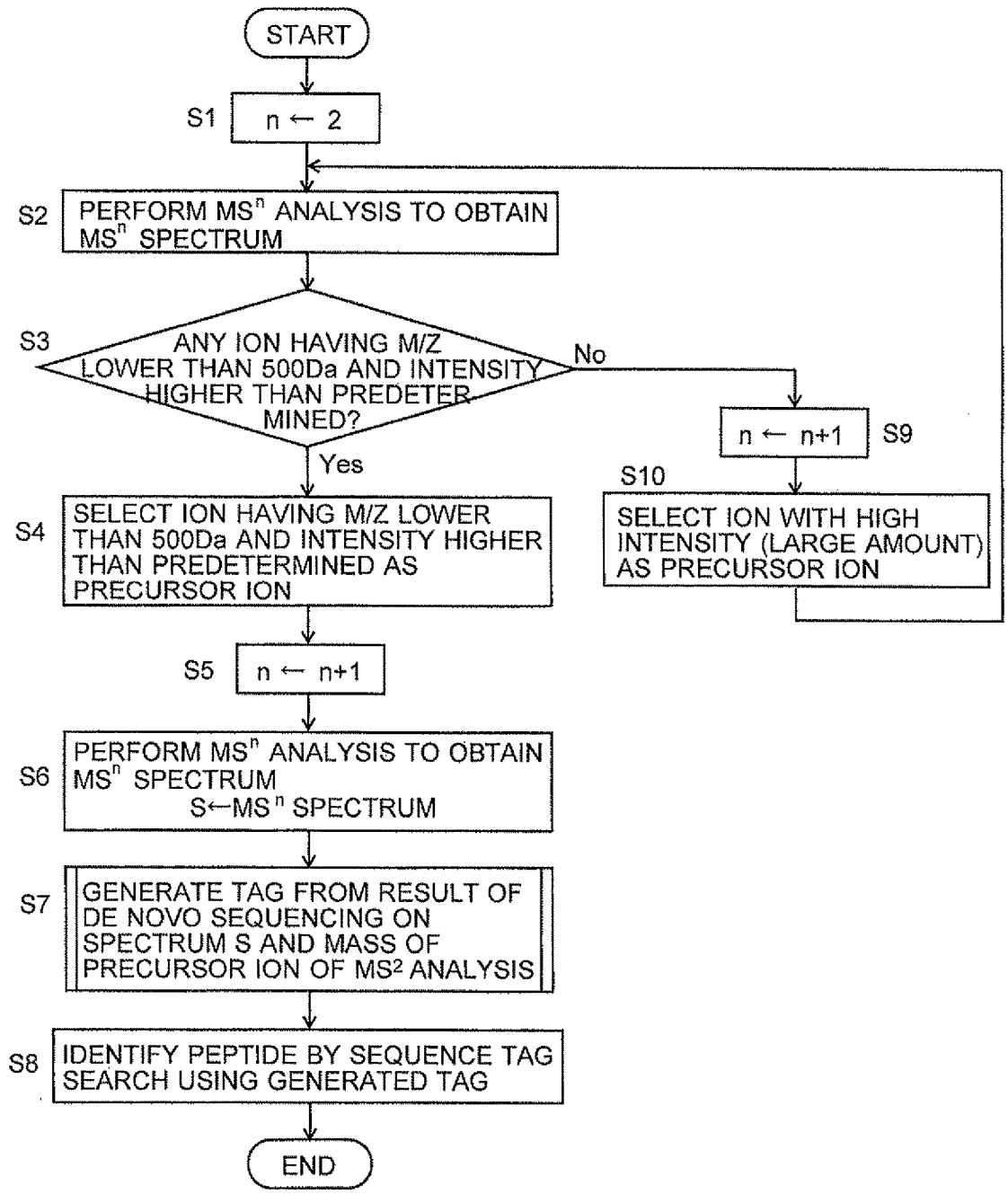
FIG. 2 is a flowchart showing one example of the data analyzing process performed in the peptide analyzing system of the present embodiment.

According to the flowchart shown in FIG. 2, the cycle of Steps S2, S3, S9 and S10 is repeated until an ion peak having a mass-to-charge ratio equal to or lower than 500 Da and an intensity equal to or higher than a specific level is found. In practice, however, repeating the cycle may result in too small a mass-to-charge ratio of the precursor ion, making it meaningless to determine the MS$^n$ spectrum. To avoid this situation, an upper limit of the parameter n, or a lower limit of the mass-to-charge ratio of the precursor ion to be selected, may be set to discontinue the repetition at an appropriate point in time and conclude that the sample is impossible to identify.

In Step S3, when it is determined that an ion peak having a mass-to-charge ratio equal to or lower than 500 Da and an intensity equal to or higher than a specific level exists in the MS$^2$ spectrum or MS$^n$ spectrum with n being equal to or greater than three, this ion peak is selected as the precursor ion (Step S4) and the parameter n is incremented by one (Step S5). Then, under the control of the analysis controller 27, the mass spectrometer unit 1 performs an MS$^n$ analysis using the selected precursor ion, and the spectrum analyzer 22 creates an MS$^n$ spectrum based on the obtained data (Step S6). For example, when the result of determination for an MS$^2$ spectrum in Step S3 has turned out to be "Yes," an MS$^3$ analysis is performed in Step S6; when the result of determination for an MS$^3$ spectrum in Step S3 has turned out to be "Yes", an MS$^4$ analysis is performed in Step S6.

Based on the MS$^n$ spectrum obtained in Step S6 and the mass-to-charge ratio of the precursor ion of the MS$^2$ analysis, the de novo sequencer 23 and the tag generator 24 generate a sequence tag (Step S7). This characteristic tag generation process is hereinafter described in detail with reference to the flowchart of FIG. 3.

The de novo sequencer 23 initially performs de novo sequencing on the MS$^n$ spectrum to deduce the amino acid sequence to be assigned to the range from the zero point of the mass to the mass-to-charge ratio of the precursor ion (Step S71). An MS$^n$ spectrum obtained by repeatedly dissociating ions normally shows clearer peaks of product ions and fewer noise peaks, which means a higher S/N ratio of the spectrum. By applying the de novo sequencing to such an MS$^n$ spectrum, a correct amino acid sequence of a portion of the entire amino acid sequence of the original peptide can be obtained. In particular, the obtained amino acid sequence will be highly reliable in the case where the amino acid sequence can be fully determined from the location of each product ion after the mass-to-charge ratio of the terminus of the amino acid sequence is corrected within a range between the mass-to-charge ratio of the precursor ion and the zero point of the mass.

After setting the parameter Str denoting the partial amino acid sequence deduced by de novo sequencing in the previously described manner and the parameter M denoting the mass-to-charge ratio of the precursor ion of the MS$^2$ analysis (Step S72), the tag generator 24 creates a sequence tag based on these parameters (Step S73). More specifically, for example, if the partial amino acid sequence Str has been deduced from an MS$^3$ spectrum in Step S71 and the mass-to-charge ratio of the precursor ion of the MS$^3$ analysis is M3, the tag generator 24 creates one sequence tag: M-tag (M3, Str, 0.0), where "0.0" means that the ending point (or starting point) of the de novo sequencing is the zero point of the mass.

If the partial amino acid sequence Str has been deduced from an MS$^4$ spectrum in Step S71 and the mass-to-charge ratios of the precursor ions used in the MS$^3$ and MS$^4$ analyses are M3 and M4, respectively, then the tag generator 24 creates not only the sequence tag M tag (M4, Str, 0.0) but also two more sequence tags: M tag (M3, Str, M3−M4+1) and M tag (M−M3+M4, Str, M−M3+1). The meanings of these two sequence tags are as follows: The mass of the neutral loss that is complementary to the precursor ion of the MS$^4$ analysis in the MS$^3$ analysis is M3−M4+1 (this "+1" is the mass of one proton). If this neutral loss appears as a peak in the MS$^3$ spectrum, the amino acid sequence which covers the range between the mass-to-charge ratio M3 of the precursor ion of the MS$^3$ analysis and the mass of this virtual neutral loss (M3−M4+1) should be Str. Therefore, the sequence tag (M4, Str, 0.0) obtained from the MS$^4$ spectrum will be the sequence tag M tag (M3, Str, M3−M4+1). Similarly, this tag can be further traced back and replaced with the sequence tag M tag (M−M3+M4, Str, M−M3+1) in the MS$^2$ spectrum.

FIG. 4 is a schematic chart showing one example of the relationship between the precursor ion of an MS$^2$ analysis, i.e. the amino acid sequence of a peptide to be identified, and an amino acid sequence derived from an MS$^4$ spectrum. This is the example of ovalbumin used in an experiment which will be described later. The amino acid sequence of the peptide corresponding to the precursor ion X of the MS$^2$ analysis is [GGLEPINFQTAADQAR], and its mass-to-charge ratio is M. In an MS$^4$ spectrum obtained by dissociating this precursor ion multiple times (two times in the present example), the product ions corresponding to an amino acid located at C-terminus of the original peptide will appear. Accordingly, if the amino acid sequence corresponding to the range between the mass-to-charge ratio M4 of the precursor ion Y and the zero point of the mass in the MS$^4$ spectrum is deduced, the result will be the amino acid sequence [QAR]. This amino acid sequence is necessarily a portion of the original peptide. Therefore, it can be understood that a sequence tag available for identifying the original peptide can be generated from the amino acid sequence, the mass-to-charge ratio M4 of the precursor ion of the MS$^4$ analysis, and the mass-to-charge ratio M of the precursor ion of the MS$^2$ analysis. As already stated, the partial amino acid sequence deduced in Step S71 is highly reliable. Therefore, the sequence tag generated in Step S73 is also highly reliable.

The description now returns to FIG. 2. One or more sequence tags obtained in Step S7 are given to the sequence tag searcher 25. Using those sequence tags, the sequence tag searcher 25 identifies the peptide by comparing the information indicated by the tags with the information registered in the identification database 26, such as the amino acid sequence and mass of the proteins (Step S8). For example, when "Mascot Sequence Query" is used as the sequence tag searcher 25, each of the peptides found by the search will be given a score, expected value or similar information indicating the reliability of the search. Accordingly, even when a plurality of peptides has been found, if there is one peptide whose reliability index is significantly higher than those of the other peptides, that peptide can be solely selected as the identified peptide. If it is impossible to select only one peptide as the identified peptide, all the peptides found by the search, together with their reliability indices, can be selected as the candidates. The identified peptide or the peptide candidates are shown on the display unit 4 to let the analysis operator know the result. In the sequence tag search, the search result necessarily includes the correct peptide as long as the concerned protein is registered in the identification database 26 and the given sequence tags are correct. That is to say, it never occurs that the search result misses a correct answer despite the presence of this answer in the database. Since the sequence tags obtained by the previously described process are highly reliable, the result of peptide identification is also highly reliable.

EXAMPLES

An evaluation experiment for confirming the effect of peptide identification by the previously described characteristic data analyzing method was conducted. This experiment used an MS$^4$ spectrum of ovalbumin and an MS$^3$ spectrum of bovine serum albumin. For each of these substances, sequence tags were generated by the previously described process, and a sequence tag search using those tags was performed to identify a peptide. For the sequence tag search, "Mascot Sequence Query" was used.

Figure 6:
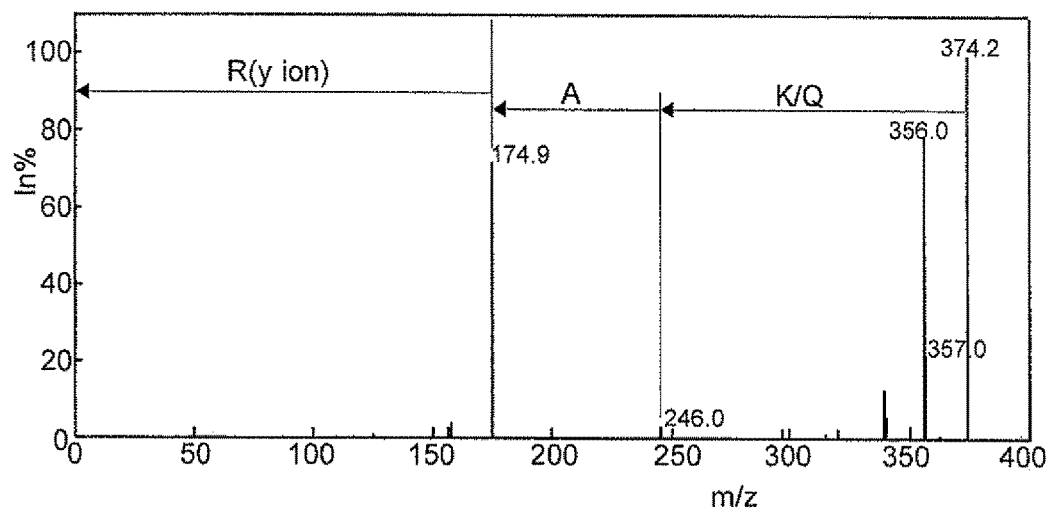
FIG. 6 is a chart showing one example of the deduction of an amino acid sequence by the de novo sequencing on an $MS^4$ spectrum of a precursor ion (m/z 374) obtained from ovalbumin.

In the experiment for ovalbumin, it was impossible to determine the amino acid sequence by the de novo sequencing on the MS$^3$ spectrum. Accordingly, one more stage of CID was added to obtain an MS$^4$ spectrum, and using this spectrum, de novo sequencing was performed to deduce the amino acid sequence covering the range from the mass-to-charge ratio of the precursor ion (m/z 374) to the zero point of the mass. The result was as shown in FIG. 6. In this figure, the mass difference between the peaks of m/z 174.9 and m/z 246.0 corresponds to alanine (A), which is an amino acid residue with a mass of 71.0. The mass difference between the zero point (m/z 0) and the peak of m/z 174.9 corresponds to the sum of Arginine (R) (mass=156.1) and OH$_3$ (mass=19).

Other than those shown in FIG. 6, there is no amino acid sequence that can be uniquely determined from the product ions corresponding to all the amino acids on the MS$^4$ spectrum. Therefore, it can be said that the amino acid sequence thus determined is highly reliable. From this amino acid sequence, a sequence tag can be generated as follows: M-tag (M4, Str, 0.0), M=1684.94, M4=374. 22 and Str="[KQ]AR", where [KQ] means either K or Q. The result of a sequence tag search using this sequence tag was as shown in FIG. 5. The list shows a plurality of even-scored candidate peptides, in which the correct peptide, i.e. ovalbumin, is included. Thus, the present example confirms that the correct peptide can be duly listed as one of the candidates by merely using one sequence tag obtained from the MS$^4$ spectrum.

Figure 7:
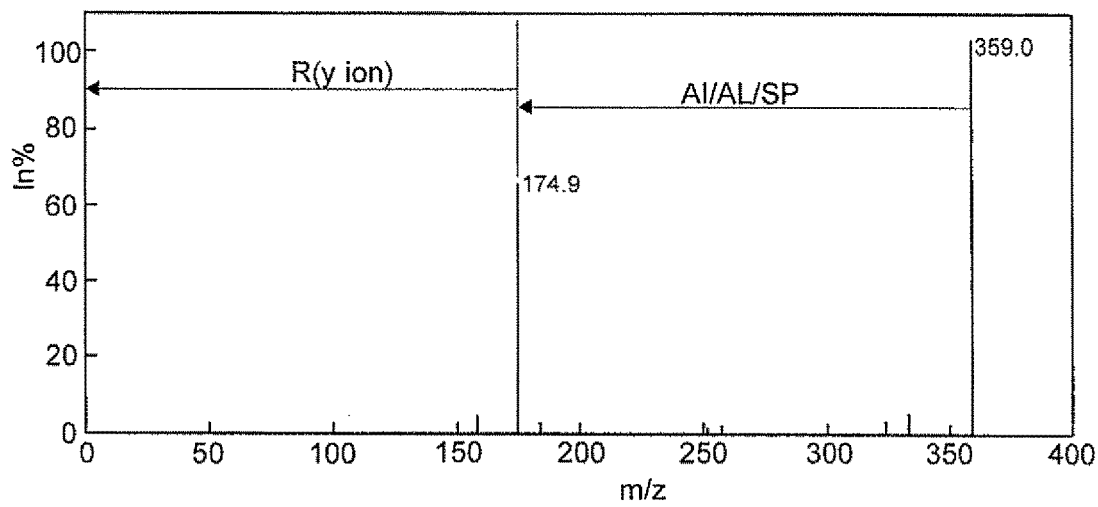
FIG. 7 is a chart showing one example of the deduction of an amino acid sequence by the de novo sequencing on an $MS^3$ spectrum of a precursor ion (m/z 359) obtained from bovine serum albumin.

FIG. 7 shows the result of an experiment in which, using an MS$^3$ spectrum of bovine serum albumin, de novo sequencing was performed to deduce the amino acid sequence covering the range from the mass-to-charge ratio of the precursor ion (m/z 359) to the zero point of the mass. Similar to the previous example, the amino acid sequence shown in FIG. 7 is the only sequence that can be uniquely determined from the product ions corresponding to all the amino acids on the MS$^3$ spectrum. This means that the amino acid sequence determined in this example is also highly reliable. From this amino acid sequence, a sequence tag can be generated as follows: M-tag (M3, Str, 0.0), M=927.5, M3=359 and Str="[AI|IA|SP|PS|AL|LA]R." The result of a sequence tag search using this sequence tag was as shown in FIG. 8. The list shows a plurality of even-scored candidate peptides, in which the correct peptide, i.e. bovine serum albumin, is included.

Figure 9A:
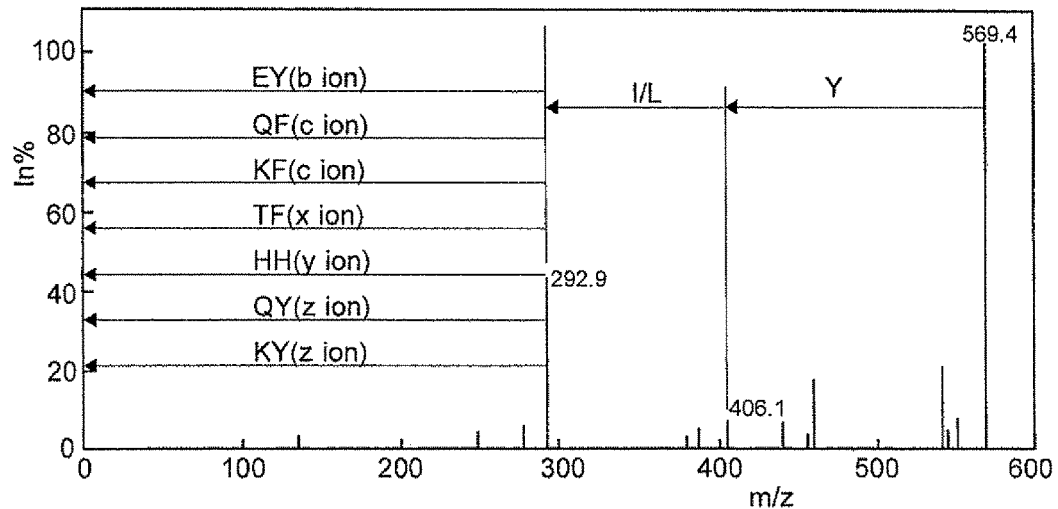
FIGS. 9A and 9B are charts showing examples of the deduction of an amino acid sequence by the de novo sequencing on an $MS^3$ spectrum of a precursor ion (m/z 569) obtained from bovine serum albumin.
Figure 9B:
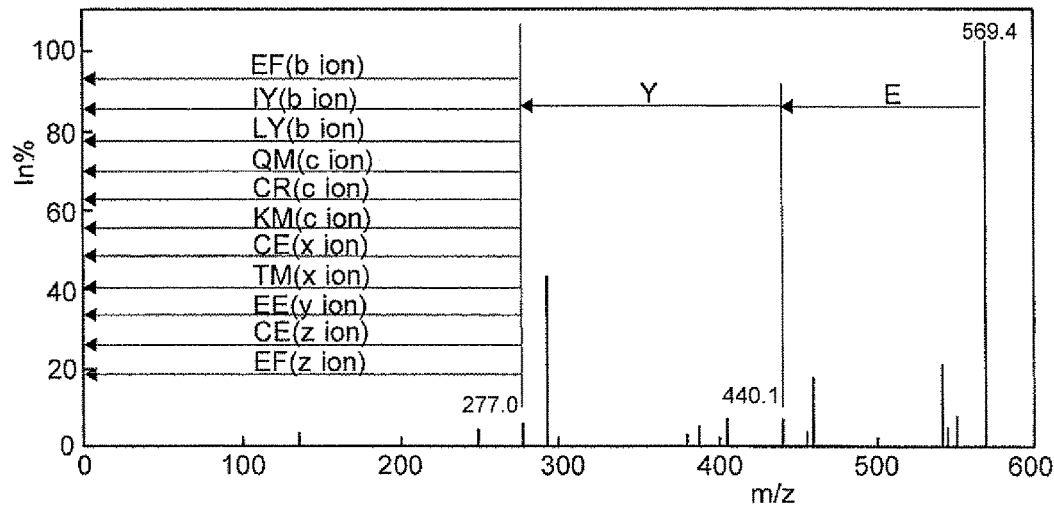
Figure 10:
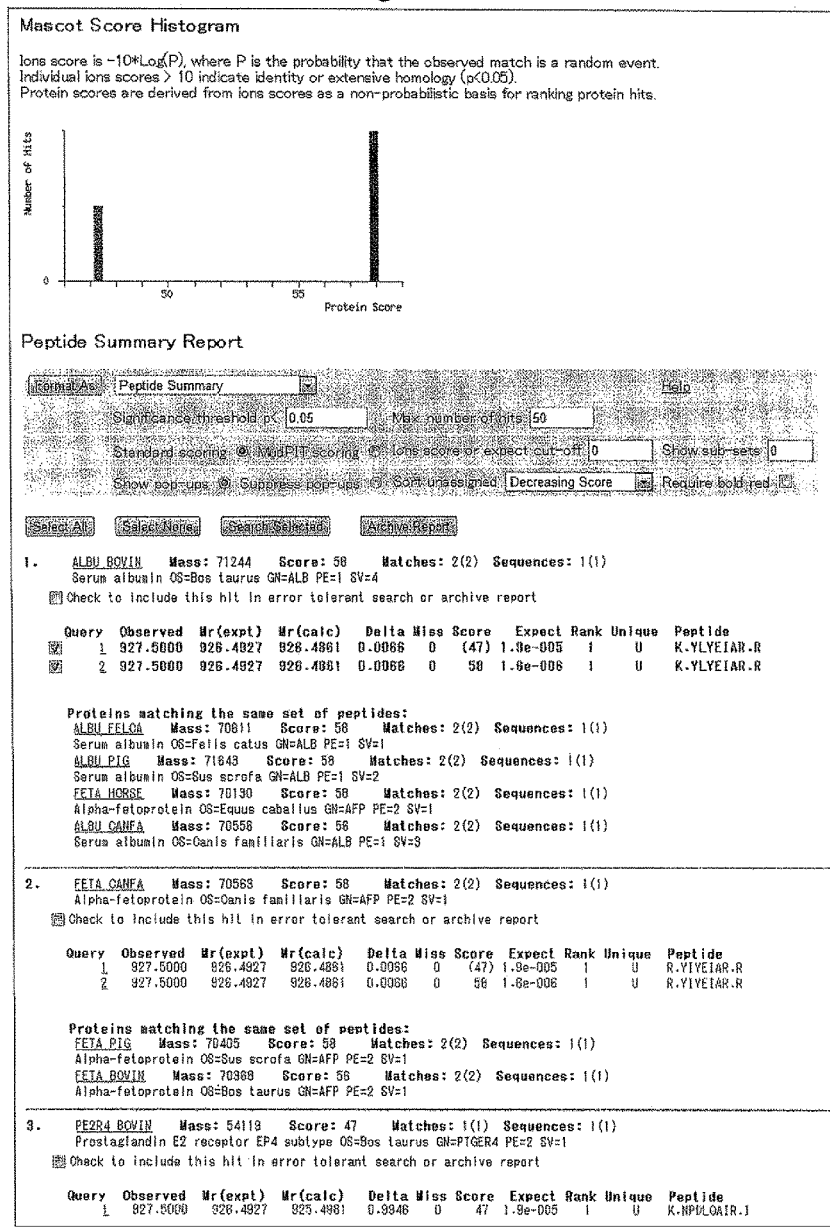
FIG. 10 is a screen shot showing a list of peptide candidates selected by "Mascot Sequence Query" using a sequence tag generated from the $MS^3$ spectrum shown in FIGS. 9A and 9B.

For the sample of bovine serum albumin, one more MS$^3$ spectrum was obtained by another MS$^3$ analysis for a precursor ion having a different mass-to-charge ratio (m/z 569). Using this MS$^3$ spectrum, the amino acid sequence covering the range from the mass-to-charge ratio of the precursor ion to the zero point of the mass was deduced by de novo sequencing. The result was as shown in FIGS. 9A and 9B. In the present example, it is impossible to uniquely determine the amino acid sequence from the product ions corresponding to all the amino acids on the MS$^3$ spectrum. However, since YLYE is the only symmetrical sequence that can be derived from the two amino acid sequences, this sequence can be used to determine the amino acid sequence with high reliability. From this deduction result of the amino acid sequence, a sequence tag different from the one obtained from the result shown in FIG. 7 can be obtained. Accordingly, a sequence tag search was conducted by using the sequence tag obtained from the result shown in FIGS. 9A and 9B as input data in addition to the sequence tag obtained from the result shown in FIG. 7. The result was as shown in FIG. 10. In the present case, since one amino acid sequence that satisfies the conditions of both sequence tags is uniquely determined, the peptide is identified with high scores. Thus, the accuracy of peptide identification can be improved by using two or more sequence tags, although the use of a single sequence tag can provide useful information in many cases.

It should be noted that the previous embodiment is a mere example of the present invention, and any change, modification or addition appropriately made within the spirit of the present invention will naturally fall within the scope of claims of this patent application.

EXPLANATION OF NUMERALS

1 . . . Mass Spectrometer Unit
10 . . . Ionizer
11 . . . Ion Trap
12 . . . Time-of-Flight Mass Spectrometer
13 . . . Flight Space 14 . . . Ion Detector
2 . . . Controlling and Processing Unit
21 . . . Data Collector
22 . . . Spectrum Analyzer
23 . . . De Novo Sequencer
24 . . . Tag Generator
25 . . . Sequence Tag Searcher
26 . . . Identification Database
27 . . . Analysis Controller
3 . . . Input Unit
4 . . . Display Unit

The invention claimed is:

1. A mass spectrometry data analyzing method for identifying a protein in a test sample containing fragments of the protein, using data collected by performing a mass spectrometry of the test sample, comprising:
a spectrum generating step, in which an $MS^n$ analysis on the test sample, where n is an integer equal to or greater than three, is performed to generate an $MS^n$ spectrum by a mass spectrometer unit coupled to a controlling and processing unit;
a partial amino acid sequence deducing step, in which de novo sequencing on the $MS^n$ spectrum is performed to determine a partial amino acid sequence;
a tag generating step, in which a sequence tag is generated by using the mass-to-charge ratio of a precursor ion of the $MS^2$ analysis, the mass-to-charge ratio of a precursor ion of the $MS^n$ analysis, and the partial amino acid sequence determined in the partial amino acid sequence deducing step; and
a database searching step, in which a database of amino acid sequence information of proteins is searched for a protein that matches information represented by the sequence tag,
wherein the precursor ion of the $MS^n$ spectrum to be used for the de novo sequencing in the partial amino acid sequence deducing step has a mass-to-charge ratio corresponding to an amino acid sequence consisting of four or less residues or has a mass-to-charge ratio of 500 Da or less.

2. The mass spectrometry data analyzing method according to claim 1, wherein:
in the partial amino acid sequence deducing step, the de novo sequencing is performed over a range starting from the mass-to-charge ratio of the precursor ion in the $MS^n$ spectrum and ending at a zero point of the mass-to-charge ratio.

3. The mass spectrometry data analyzing method according to claim 2, wherein:
the partial amino acid sequence deducing step includes determining a plurality of partial amino acid sequences by performing de novo sequencing on each of a plurality of $MS^n$ spectra respectively obtained for two or more different precursor ions;
the tag generating step includes generating a plurality of sequence tags respectively corresponding to the partial amino acid sequences determined in the partial amino acid sequence deducing step; and
the database searching step includes searching for a protein by a database search using the plurality of sequence tags.

4. A mass spectrometry data analyzing method for identifying a protein in a test sample containing fragments of the protein, using data collected by performing a mass spectrometry of the test sample, comprising:
a spectrum generating step, in which an $MS^n$ analysis on the test sample, where n is an integer equal to or greater than three, is performed to generate an $MS^n$ spectrum by a mass spectrometer unit coupled to a controlling and processing unit;
a partial amino acid sequence deducing step, in which de novo sequencing on the $MS^n$ spectrum is performed to determine a partial amino acid sequence;
a tag generating step, in which a sequence tag is generated by using the mass-to-charge ratios of precursor ions used in $MS^m$ analyses (where m is all integers equal to or greater than two and equal to or less than n) and the partial amino acid sequence determined in the partial amino acid sequence deducing step; and
a database searching step, in which a database of amino acid sequence information of proteins is searched for a protein that matches information represented by the sequence tag,
wherein the precursor ion of the $MS^n$ spectrum to be used for the de novo sequencing in the partial amino acid sequence deducing step has a mass-to-charge ratio corresponding to an amino acid sequence consisting of four or less residues or has a mass-to-charge ratio of 500 Da or less.

5. The mass spectrometry data analyzing method according to claim 4, wherein:
in the partial amino acid sequence deducing step, the de novo sequencing is performed over a range starting from the mass-to-charge ratio of the precursor ion in the $MS^n$ spectrum and ending at a zero point of the mass-to-charge ratio.

6. The mass spectrometry data analyzing method according to claim 5, wherein: the partial amino acid sequence deducing step includes determining a plurality of partial amino acid sequences by performing de novo sequencing on each of a plurality of $MS^n$ spectra respectively obtained for two or more different precursor ions;
the tag generating step includes generating a plurality of sequence tags respectively corresponding to the partial amino acid sequences determined in the partial amino acid sequence deducing step; and
the database searching step includes searching for a protein by a database search using the plurality of sequence tags.

7. A mass spectrometry data analyzing system for identifying a protein in a test sample containing fragments of the protein, using data collected by performing a mass spectrometry of the test sample, comprising:
a mass spectrometer unit coupled to a controlling and processing unit for performing an $MS^n$ analysis on the test sample, where n is an integer equal to or greater than three, to generate an $MS^n$ spectrum;
the controlling and processing unit comprising:
a partial amino acid sequence deducing step for performing de novo sequencing on the $MS^n$ spectrum to determine a partial amino acid sequence;
a tag generating step for generating a sequence tag by using the mass-to-charge ratio of a precursor ion of the $MS^2$ analysis, the mass-to-charge ratio of a precursor ion of the $MS^n$ analysis, and the partial amino acid sequence determined by the partial amino acid sequence deducing step; and
a database searching step for searching a database of amino acid sequence information of proteins for a protein that matches information represented by the sequence tag,
wherein the precursor ion of the $MS^n$ spectrum to be used for the de novo sequencing by the partial amino acid sequence deducing step has a mass-to-charge ratio corresponding to an amino acid sequence consisting of four or less residues, or has a mass-to-charge ratio of 500 Da or less.

8. The mass spectrometry data analyzing system according to claim 7, wherein:
the partial amino acid sequence deducing step performs the de novo sequencing over a range starting from the mass-to-charge ratio of the precursor ion in the $MS^n$ spectrum and ending at a zero point of the mass-to-charge ratio.

9. The mass spectrometry data analyzing system according to claim 8, wherein:
the partial amino acid sequence deducing step determines a plurality of partial amino acid sequences by performing de novo sequencing on each of a plurality of $MS^n$ spectra respectively obtained for two or more different precursor ions;
the tag generating step generates a plurality of sequence tags respectively corresponding to the partial amino acid sequences determined in the partial amino acid sequence deducing step; and
the database searching step searches for a protein by a database search using the plurality of sequence tags.

10. A mass spectrometry data analyzing system for identifying a protein in a test sample containing fragments of the protein, using data collected by performing a mass spectrometry of the test sample, comprising:
a mass spectrometer unit coupled to a controlling and processing unit for performing an $MS^n$ analysis on the test sample, where n is an integer equal to or greater than three, to generate an $MS^n$ spectrum;
said controlling and processing unit comprising;
a partial amino acid sequence deducing step for performing de novo sequencing on the $MS^n$ spectrum to determine a partial amino acid sequence;
a tag generating step for generating a sequence tag by using the mass-to-charge ratios of precursor ions used in $MS^m$ analyses, where m is all integers equal to or greater than two and equal to or less than n, and the partial amino acid sequence determined by the partial amino acid sequence deducing section step; and
a database searching step for searching a database of amino acid sequence information of proteins for a protein that matches information represented by the sequence tag,
wherein the precursor ion of the $MS^n$ spectrum to be used for the de novo sequencing by the partial amino acid sequence deducing step has a mass-to-charge ratio corresponding to an amino acid sequence consisting of four or less residues or has a mass-to-charge ratio of 500 Da or less.

11. The mass spectrometry data analyzing system according to claim 10, wherein:
the partial amino acid sequence deducing step performs the de novo sequencing over a range starting from the mass-to-charge ratio of the precursor ion in the $MS^n$ spectrum and ending at a zero point of the mass-to-charge ratio.

12. The mass spectrometry data analyzing system according to claim 11, wherein:
the partial amino acid sequence deducing step determines a plurality of partial amino acid sequences by performing de novo sequencing on each of a plurality of $MS^n$ spectra respectively obtained for two or more different precursor ions;
the tag generating step generates a plurality of sequence tags respectively corresponding to the partial amino acid sequences determined in the partial amino acid sequence deducing step; and
the database searching step searches for a protein by a database search using the plurality of sequence tags.

* * * * *